United States Patent
Marchal (10) Patent No.: US 6,612,983 B1
(45) Date of Patent: Sep. 2, 2003

(54) PANCREATIC SECRETION RESPONSE TO STIMULATION TEST PROTOCOL

(75) Inventor: Benoit Marchal, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/535,840

(22) Filed: Mar. 28, 2000

(51) Int. Cl.[7] .............................. A61B 5/00; A61B 19/00
(52) U.S. Cl. ..................... 600/300; 600/554; 607/40; 607/133; 128/898
(58) Field of Search .................... 600/300, 301, 600/436, 554; 128/897–925; 607/40, 133

(56) References Cited

U.S. PATENT DOCUMENTS

| | | | |
|---|---|---|---|
| 3,719,183 A | 3/1973 | Schwartz | 128/2 R |
| 4,279,886 A | 7/1981 | Allen | 424/1 |
| 5,188,104 A | 2/1993 | Wernicke et al. | 128/419 R |
| 5,231,988 A | 8/1993 | Wernicke et al. | 128/421 |
| 5,263,480 A | 11/1993 | Wernicke et al. | 607/118 |
| 5,425,751 A | 6/1995 | Baeten et al. | 607/28 |
| 5,699,739 A | * 12/1997 | Brasile et al. | 600/300 |
| 5,716,392 A | 2/1998 | Bourgeois et al. | 607/132 |
| 5,836,994 A | 11/1998 | Bourgeois | 607/40 |
| 5,861,014 A | 1/1999 | Familoni | 607/40 |
| 5,919,216 A | 7/1999 | Houben et al. | 607/72 |

FOREIGN PATENT DOCUMENTS

WO    WO 88/03389    5/1988

OTHER PUBLICATIONS

Chen et al., Serosal and Cutaneous Recordings of Gastrc Myoelectrical Activity in Patients with Gastroparesis, Jan. 1994, American Journal of Physiology, vol. 266, Pt. 1, p90–98.*

Richins, "the Innervation of the Pancreas," J. Comp. Neurol 82:223–236 (1945).

Netter, Frank, "The Ciba Collection of Medical Illustrations," vol. 3 Digestive System, Part III Liver, Billary Tract and Pancreas (1964).

Kang, Sharon Y., et al., "Pancreatic Exocrine–Endocrine Interrelationship, Clinical Implications", Pancreas Update 0889–8553 (Sep., 1999), vol. 28, No. 3.

Holst, Jens et al., "Nervous Control of Pancreatic Secretion in Pigs", Acta Physiol. Scand. 105, 33–51 (1979).

(List continued on next page.)

*Primary Examiner*—Eric F. Winakur
*Assistant Examiner*—David McCrosky
(74) *Attorney, Agent, or Firm*—Thomas F. Woods (57) ABSTRACT

A screening test is used on a patient to determine if pancreatic secretion is responsive to stimulation. The screening test compares measurements of a pancreatic indicator both before and after natural stimulation. The pancreatic indicator is measured before natural stimulation and then the patient's pancreas is naturally stimulated. After waiting a time period from when the natural stimulation began, the pancreatic indicator is once again measured. The difference between the pancreatic indicator measured before ingesting the meal and the pancreatic response indicator measured after ingesting and waiting a time period is calculated and a decision is made whether the patient has a pancreatic condition suitable for treatment with electrical stimulation. Additionally, an efficacy test is used to evaluate the efficacy of employing electrical stimulation to treat a pancreatic condition. Electrical stimulation is administered with a gastroelectric stimulator having a neurostimulator, an electrical lead, and electrodes placed in the patient's abdomen at a location to stimulate the patient's pancreas. The efficacy test compares a pancreatic response indicator before electrical stimulation and after electrical stimulation to decides whether there is efficacy in using electrical stimulation to treat a patient's pancreatic condition.

32 Claims, 11 Drawing Sheets

OTHER PUBLICATIONS

Fiorucci et al., "Duodenal Osmolality Drives Gallbladder Emptying in Humans, Digestive Diseases and Sciences", vol. 35. No. 6, pp. 698–704 (Jun. 1990).

Koch, Kenneth et al., Electrogastrography, An Illustrated Guide to Gastrointestinal Motility $2^{nd}$ Ed., pp. 290–307 (1993).

* cited by examiner

PANCREATIC SECRETION RESPONSE TO STIMULATION TEST PROTOCOL

BACKGROUND OF THE INVENTION

This disclosure relates to a medical test and more specifically to a test protocol for assessing a patient's pancreatic response to natural and electrical stimulation.

The medical device industry produces a wide variety of electronic and mechanical devices for treating patient medical conditions. Depending upon medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life. One type of medical device that can be used to treat pancreatic conditions is a neurostimulator. Neurostimulator treatment for pancreatic conditions involves placing electrical leads typically within the gastrointestinal tract of a patient and applying an electrical signal with an implanted or external neurostimulator. When considering whether neurostimulation would be suitable to treat a condition in a patient, patient testing is helpful.

Pancreatic testing is challenging because the pancreas is a complex organ with a multitude of functions and many pancreatic conditions manifest themselves indirectly through symptoms that may not initially be attributed to a pancreatic condition. Pancreatic testing is also challenging because the pancreas is not a static organ that secretes at a constant rate. Pancreatic secretion varies in response to a variety of factors that may stimulate or decrease pancreatic secretions. Some conditions attributable to pancreatic dysfunction are: pancreatitis, diabetes, inflammation of the pancreas, malabsorbtion syndrome, and certain cancers. In addition to these conditions, there are a variety of other conditions that may be attributable to pancreatic dysfunction such as pain, nausea, and vomiting.

Previous pancreatic diagnostic tests are static and involve measuring one or more pancreatic function indicators and then correlating the measurements to measurements expected for various types of pancreatic disease. An example such static pancreatic testing is described in the following publication: Frank Netter, "The Ciba Collection of Medical Illustrations", Vol. 3 Digestive System, Part III Liver, Billary Tract And Pancreas (1964). Static testing does not evaluate pancreatic response to stimulation so some pancreatic conditions may not be identified.

For the foregoing reasons, there is a need for a pancreatic test that evaluates pancreatic response to stimulation. Additionally, pancreatic testing in response to stimulation would provide additionally information that would be helpful in selecting a therapy such as electrical stimulation to treat a pancreatic condition and avoid inappropriate therapies, so patients' benefit from decreased risk of medical complications, reduced pain, more rapid treatment, and reduced costs.

SUMMARY OF THE INVENTION

A screening test is used on a patient to determine if pancreatic secretion is responsive to stimulation. The screening test compares measurements of a pancreatic indicator both before and after natural stimulation. The pancreatic indicator is measured before natural stimulation and then the patient's pancreas is naturally stimulated. After waiting a time period from when the natural stimulation began, the pancreatic indicator is once again measured. The difference between the pancreatic indicator measured before ingesting the meal and the pancreatic response indicator measured after ingesting and waiting a time period is calculated and a decision is made whether the patient has a pancreatic condition suitable for treatment with electrical stimulation.

In one version of the invention, an efficacy test is used to evaluate the efficacy of employing electrical stimulation to treat a pancreatic condition. The efficacy test compares a pancreatic response indicator before electrical stimulation and after electrical stimulation to decides whether there is efficacy in using electrical stimulation to treat a patient's pancreatic condition. In other version of the invention, an efficacy test is used to evaluate the efficacy of using electrical stimulation to treat nausea and vomiting.

DETAILED DESCRIPTION OF THE PREFERRED EMBODIMENTS

Figure 1:
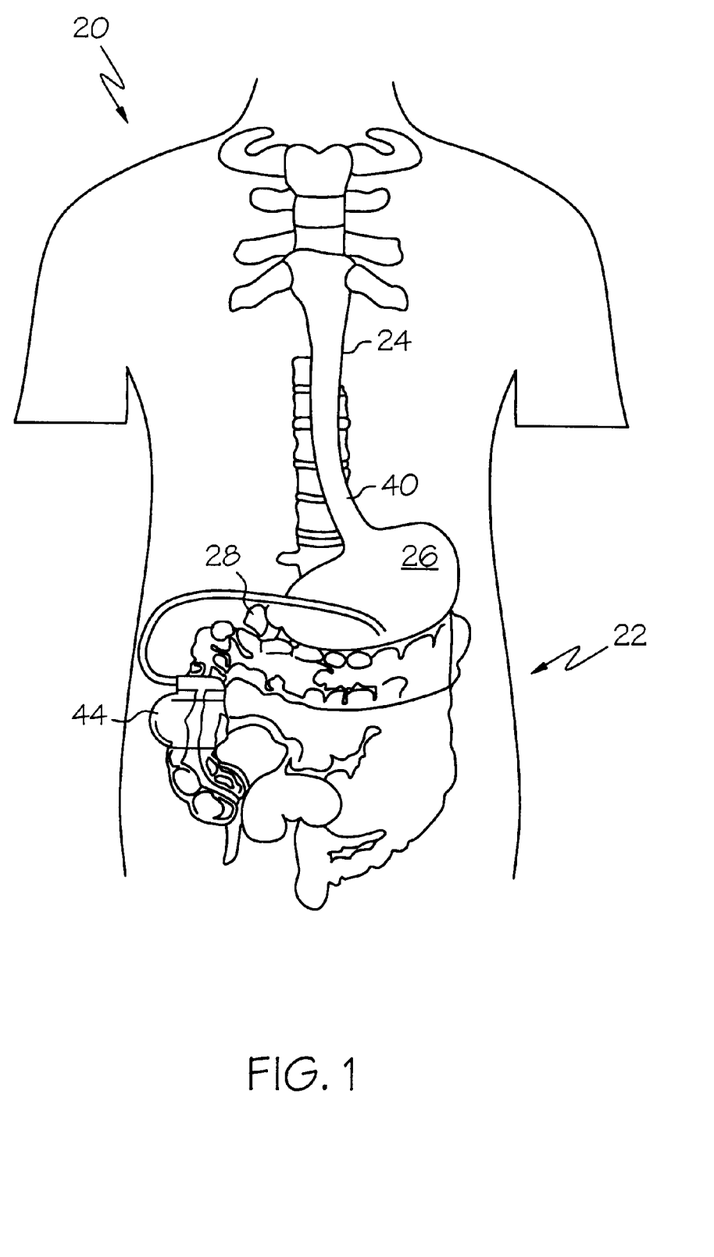
FIG. 1 shows an environment of a pancreatic test.
Figure 2:
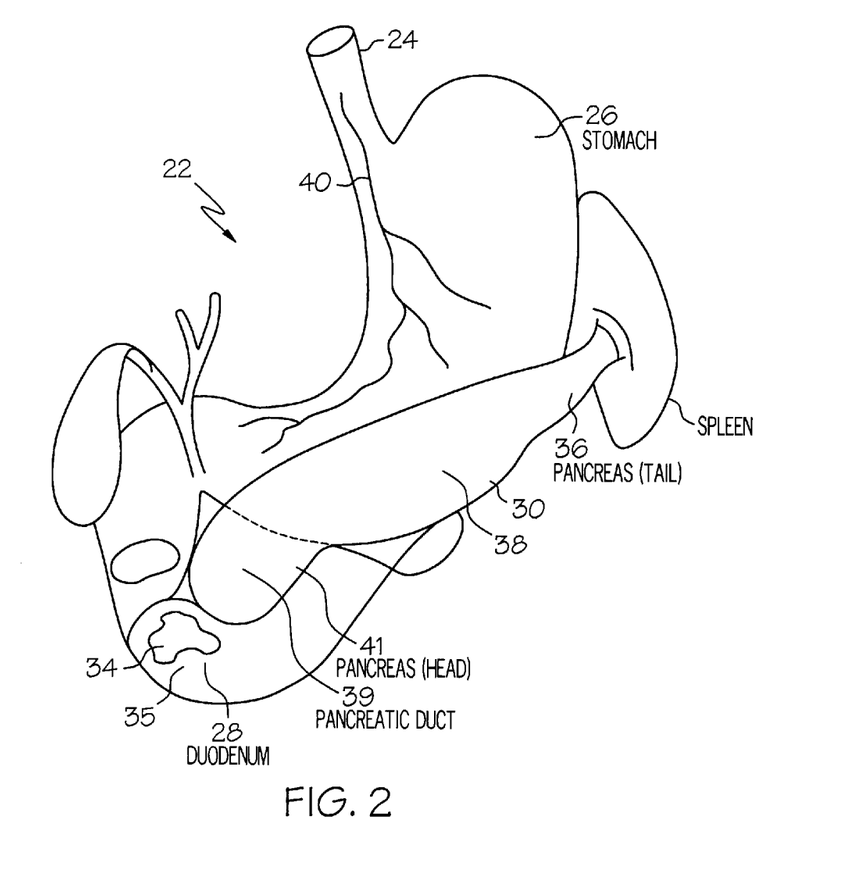
FIG. 2 shows a more detailed environment for a pancreatic test.

FIGS. 1 and 2 show the general environment for pancreatic testing. A patient's 20 digestive system 22 includes the esophagus 24, stomach 26, duodenum 28, and pancreas 30. The stomach 26 plays a role in influencing the digestive system 22 by acting as a pacemaker through myoelectrical activity as described in the following publication: Kenneth Koch et al., Electrogastrography, An Illustrated Guide To Gastrointestinal Motility $2^{nd}$ Ed., pp. 290–307 (1993).

The duodenum 28 is the first division of the small intestine that is about 25.0 cm in length and includes the pars descendens into which the pancreatic 30 ducts open. Duodenal chyme 34 is a semi-fluid mass of partly digested food with a typical normal daily volume of about 4.0 to 7.0 liters that passes from the stomach 26 into the duodenum 28. The duodenum 28 has osmoreceptors 35 that respond to osmotic pressure in the duodenum 28 by sending nerve impulses that can cause nausea and vomiting when the osmoreceptors 35 sense a significant osmotic imbalance in the duodenum 28.

The pancreas 30 has a tail 36, a body 38, a head 41, a duct of Santorini and a duct 39 of Wirsung. The duct 39 of Wirsung is the principal duct that drains most of the gland that starts in the tail 36 by the confluence of several small ducts and extends into the head 41 where it terminates at the duodenum 28 papilla. The duct of Santorini is an accessory duct that drains a small upper anterior part of the head 41 and terminates in the duodenum 28 at a small accessory papilla. The exocrine pancreas 30 has acini cells and a ductal system of intralobular and intercalated ducts organized into lobules that secrete enzymes and bicarbonate into the duodenum 28 where they aid in digestion and absorption of nutrients. Pancreatic 30 interdigestive secretion cycles are in temporal coordination with gastrointestinal motility. Pancreatic 30 secretions include exocrine and endocrine secretions that are dominantly isotonic.

Pancreatic 30 exocrine secretions mainly assist in digestion and include bicarbonate and enzymes such as trypsin, chymotrypsin, amylase, and lipase. Daily pancreatic exocrine secretion is typically in the range from 1.0 to 2.0 liters. Pancreatic 30 endocrine secretion regulate metabolism and include enzymes such as insulin, glucagons, somatostatin, and pancreatic polypeptide. Pancreatic 30 secretions are responsive to nervous control and gut hormones.

The pancreas 30 and other intra-abdominal organs are innervated by the sympathetic and parasympathetic branches of the autonomic nervous system. Sympathetic innervation is supplied by the splanchnic nerves, and parasympathetic innervation is supplied by the vagus nerves 40. Pancreatic 30 acinar and islet cells are innervated only directly through parasympathetic nerves, and pancreatic 30 blood vessels are innervated solely by sympathetic nerves. All nerves of the pancreas 30, both afferent and efferent, pass through the celiac plexus. Pancreatic 30 secretion can be affected by both natural simulation and electrical stimulation. Pancreatic 30 exocrine and endocrine secretion are controlled by the central and enteric nervous system and by gut hormones that are released after meal ingestion. Pancreatic 30 innervation is further described in the following article by Richins, "The innervation of the pancreas", J. Comp. Neurol 82:223–236 (1945). Pancreatic 30 secretion can also be influenced by electrical stimulation.

Electrical stimulation applied to nerves innervating the pancreas 30, organs commonly innervated, or the pancreas 30 itself can influence pancreatic secretions. When electrical stimulation is applied to nerves, existing natural signals can be blocked or altered as described in Durand, Dominique M., "Electric Stimulation of Excitable Tissue", The Biomedical Engineering Handbook, Chapter. 17, pp. 229–251 (1995). One location to apply electrical stimulation to influence pancreatic 30 secretions is the stomach 26 because the stomach 26 shares significant common innervation with the pancreas 30.

Figure 3:
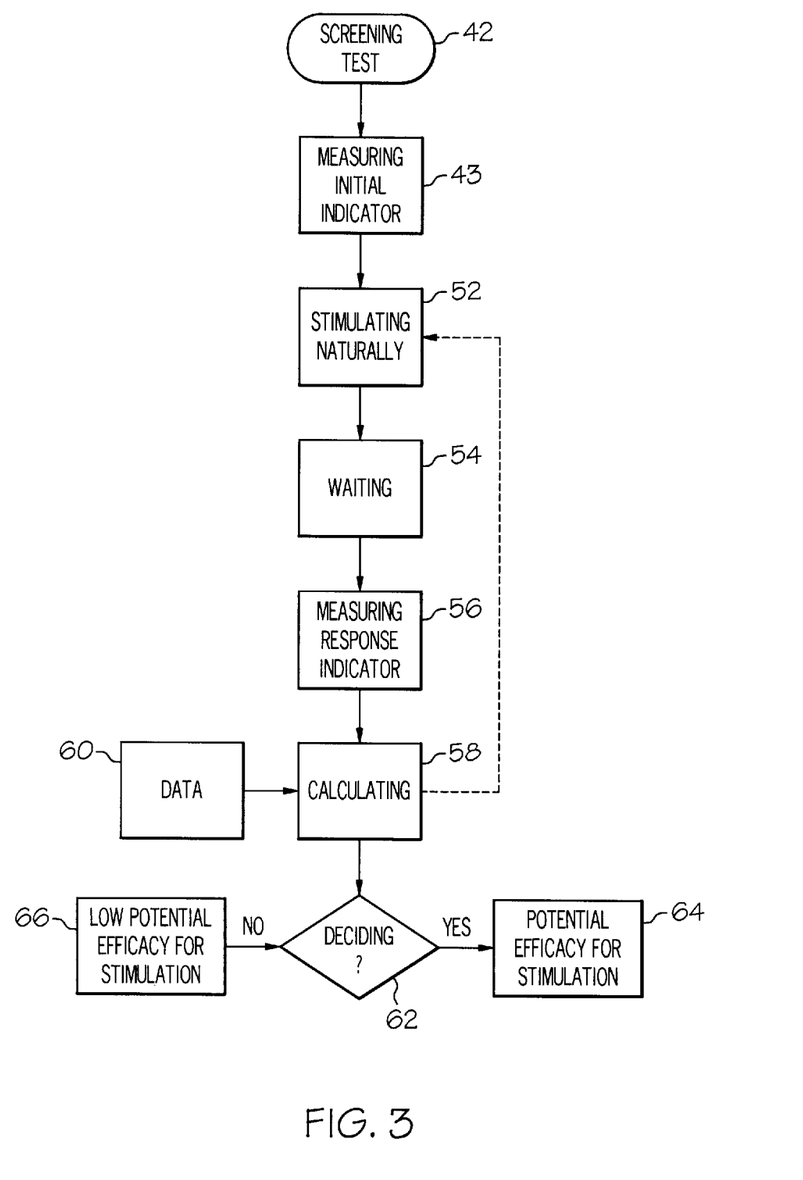
FIG. 3 shows a flow diagram for a screening test for pancreatic secretion in response to stimulation.
Figure 9:
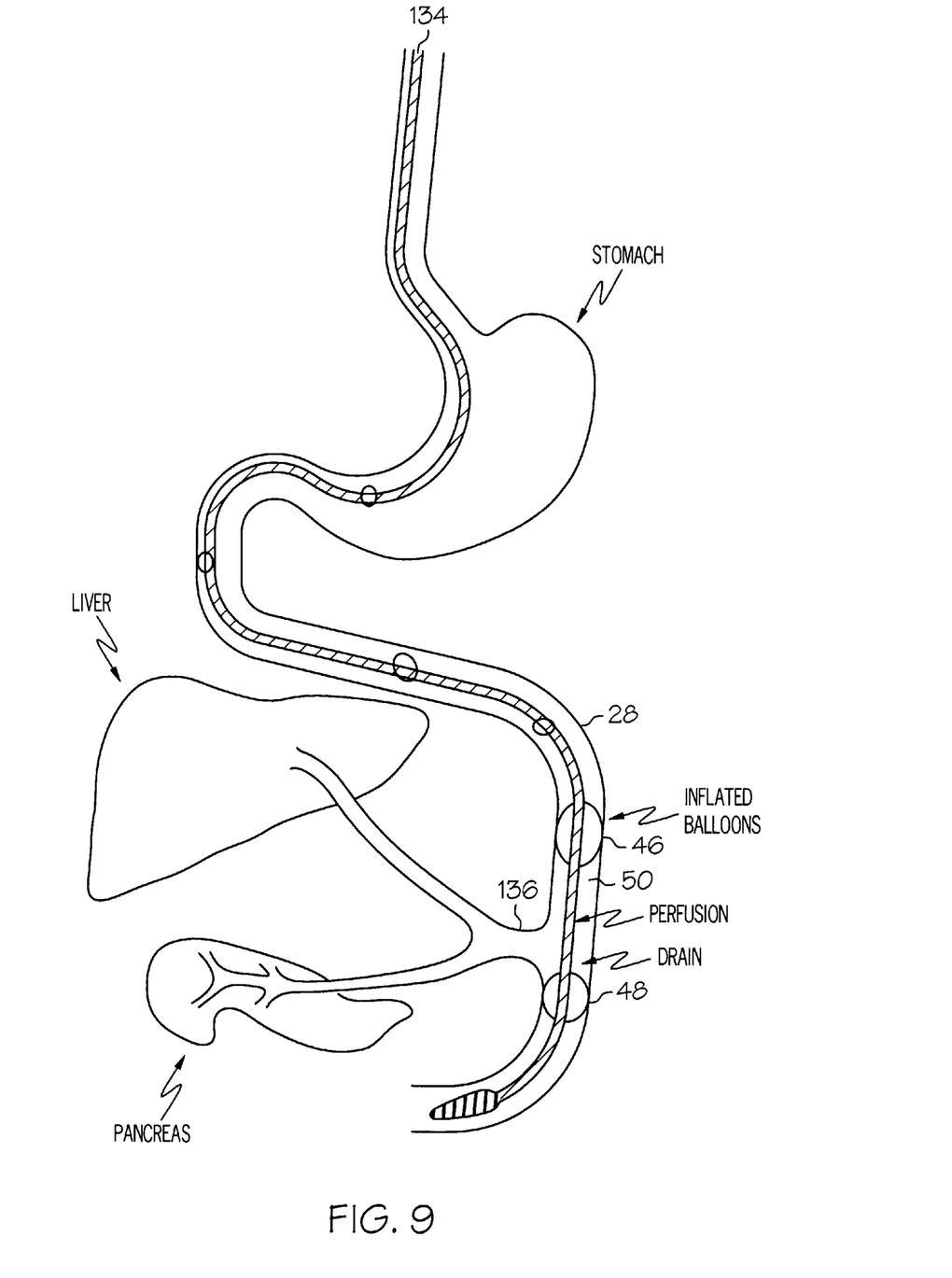
FIG. 9 shows a catheter positioned to perform the efficacy test to treat emesis; and, FIG. 10 shows a timing diagram of the efficacy test for treating emesis.

FIG. 3 shows a flow diagram depicting a screening test method 42 for using gastroelectric stimulation to affect pancreatic 30 (FIG. 2) secretion in a patient 20. The purpose of the screening test 42 is to determine whether there is potential efficacy in using a gastroelectric stimulator 44 (FIG. 1) to affect pancreatic 30 secretions in a patient 20, so ineffective therapies can be avoided. Patients 20 benefit from avoiding inappropriate therapies from a decreased risk of medical complications, reduced pain, more rapid treatment, and lower costs. The method 42 comprises the following elements. First, a initial pancreatic 30 response is measured at step 43 to establish a starting point. Pancreatic 30 response can be measured directly from duodenal pancreatic 30 secretion or indirectly with a pancreatic 30 secretion indicator. Duodenal pancreatic 30 secretion can be measured with a catheter such as shown in PCT Patent Application No. WO 88/03389 by Haillgren et al. titled "Catheter And Method For Intestinal Aspiration, Perfusion and Provocation And Its Use In The Diagnosis Of Intestinal Disease/Allergy" (1988). FIG. 9 shows the patient's duodenum 28 isolated with an upstream occlusion 46 and a downstream occlusion 48 that create a duodenal isolation area 50 in the duodenum 28. Pancreatic 30 secretion that occurs in the isolation area 50 is evacuated and the volume is measured to calculate pancreatic 30 response. Duodenal pancreatic 30 secretion measurement is discussed in more detail in below under FIGS. 8–9. Pancreatic 30 secretion response can also be measured with a pancreatic 30 secretion indicator.

A pancreatic 30 secretion indicator is a substance that varies in the body in relation to pancreatic 30 stimulation and are typically found in a patient's blood and/or stool. There is an interrelationship between pancreatic 30 exocrine and endocrine indicators that underlie numerous pancreatic 30 disorders, so measurement of an exocrine indicator can reflect on both pancreatic 30 exocrine and endocrine function; likewise, measurement of an endocrine indicator can reflect on both pancreatic 30 endocrine and exocrine function. This interrelationship is further described in the following article: Sharon Kang et al., "Pancreatic Exocrine-Endocrine Interrelationship, Clinical Implications", Pancreas Update 0889–8553 (1999). Some of the response indicators that can be used are pancreatic 30 exocrine or endocrine secretions such as pancreatic polypeptide and elastase. Additionally, a response indicator can be a substance that is not an exocrine or endocrine secretion but still varies according to pancreatic 30 secretion such as stool fat. Pancreatic 30 polypeptide is an endocrine hormone measured by blood sampling that has been found to be a good indicator of the level of vagal 40 (FIG. 1) stimulation of the pancreas 30. Typically pancreatic 30 polypeptide oscillates at baseline level, increases by four to five-fold after a meal and then returns to baseline level about three to four hours after the meal. Ingestion of food causes stimulation of the pancreas 30 perhaps by the vagal nerve 40. A patient with a vagatomy, surgical severing of the vagal nerve 40, would not be expected to have an increase in pancreatic 30 polypeptide after ingesting food. After measuring initial pancreatic 30 response, pancreatic 30 secretion is stimulated naturally.

Naturally stimulating 52 the patient's pancreas 30 is done with sensory stimulation that naturally occurs to cause an increase in pancreatic 30 secretion such as looking at food, smelling food, or eating food. After the natural stimulation 52, a natural response time 54 is waited to allow for the lag between pancreatic 30 stimulation and a change in the pancreatic 30 response. The natural response time 54 is the time necessary for the pancreatic 30 response to accurately represent pancreatic 30 secretion such as a time period of about 15.0 minutes. After the natural response time 54 has been waited, the pancreatic 30 response can be measured.

Next, the pancreatic response is once again measured 56 after waiting the natural response time 54. Now the difference between the initial pancreatic response 44 and the subsequent response 56 are calculated 58. When this calculation 58 is performed, previously established predetermined screening data 60 can be considered to improve the accuracy of the measurement. The predetermined screening data 60 is data that will improve the accuracy or reliability of the pancreatic 30 response measurement such as statistically data from previous testing, or a previous screening test 42 run on the current patient being tested.

Once the calculation 58 is performed, a decision 62 about the potential for efficacy in using a gastroelectric stimulator 44 can be made. Generally it is theorized that there is potential stimulation efficacy 64 if natural stimulation 52 increases pancreatic 30 response, but the increased response is less that what would normally be expected under the conditions. Generally it is theorized that there is little or no potential stimulation efficacy 66 if natural stimulation increases pancreatic 30 response to a normal level that would be expected under the conditions. Also, there is little or no potential stimulation efficacy 66 if natural stimulation 52 does not increase pancreatic 30 response.

Figure 4:
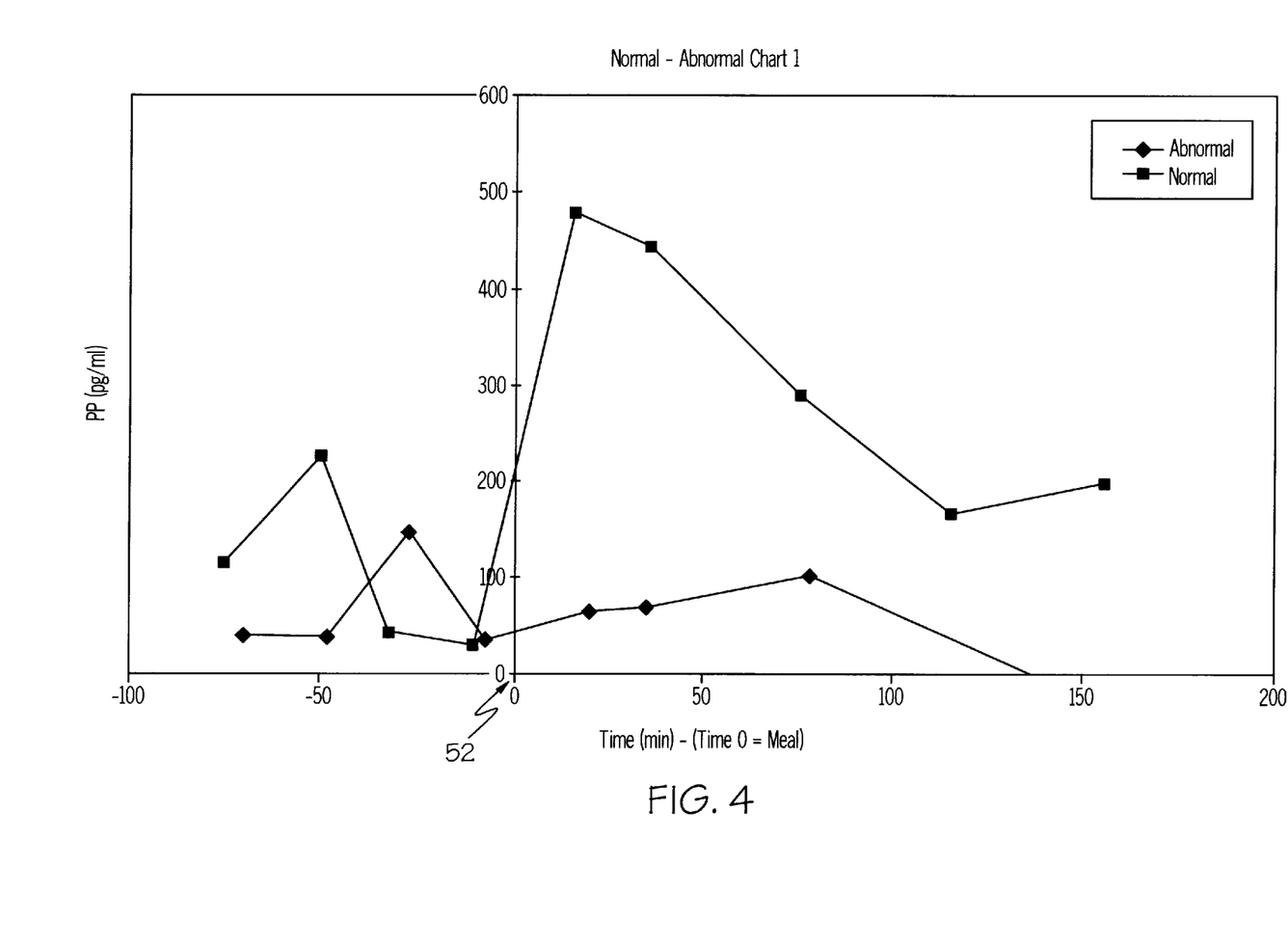
FIG. 4 shows a graph of results from the screening test.

FIG. 4 shows polypeptide level for two different patients 20 undergoing the screening test 42 for using gastroelectric stimulation to affect pancreatic 30 secretion as discussed under FIG. 3. Natural pancreatic stimulation 52 occurs at t=0. The first patient 68 shows a normal polypeptide excursion after natural stimulation 52. The second patient 70 shows an abnormal polypeptide excursion after natural stimulation 52. The first patient's 68 polypeptide levels are normal because the levels increased after natural stimulation 52 and then for an additional two to three hours. The second patient's 70 polypeptide levels are abnormal because the levels are generally flat.

Figure 5:
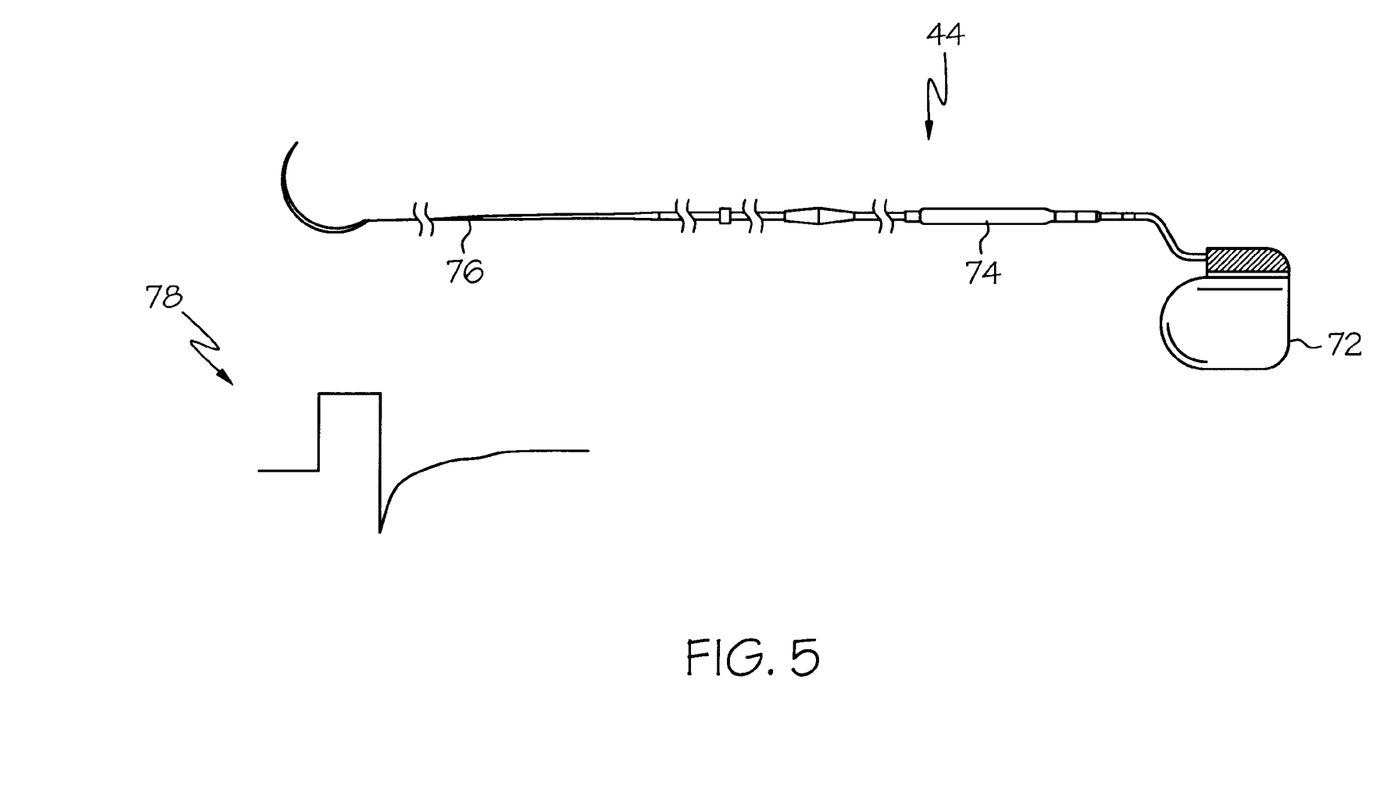
FIG. 5 shows a diagram of a gastroelectric stimulator.

FIG. 5 shows a diagram of a gastroelectric stimulator 44 that includes a neuroelectrical stimulator 72, an electrical lead 74, and electrical contacts 76 also known as electrodes 76. The neurostimulator 72 produces a stimulation signal 78 that can be used to perform neuromodulation at to reduce pain, decrease tremors, control incontinence, and perform other medical therapies. The neurostimulator 72 can be programmed to adjust stimulation signal 78 parameters such as pulse width, frequency, amplitude, polarization, and duration. The neuroelectrical stimulator 72 can be surgically implanted in a subcutaneous pocket in the abdomen or attached to the patient 20. The neuroelectrical stimulator 72 can be a device such as an Itrel® 3 Model 7425 available from Medtronic, Inc. in Minneapolis, Minn. The neurostimulator 72 is typically programmed with a physician programmer such as a Model 7432 also available from Medtronic, Inc.

The electrical lead 74 provides an electrical path for the stimulation signal 78 from the neurostimulator 72 to the electrodes 76. The electrical lead 74 is a lead suitable for a neurostimulator 72 such as Model 4300 leads available from Medtronic, Inc. The electric leads 74 can be surgically implanted into the muscle wall of the stomach 26 such as 0.5–10.0 cm apart on the greater curvature at the limit of the corpus-antrum using a surgical technique such as laparotomy or laparoscopy. The lead 74 can be placed in the lesser curvature of the corpus via a preexisting percutaneous gastrostomy site. The electrical lead 74 and electrical contacts 76 are selected with an impedance to produce a pulse current in the range from about 1.0 to 10.0 mA. The distal end the electrical lead 74 carries electrical contacts 76.

The electrical contacts 76 comprise at least two electrodes 76 and additional electrodes 76 can be used. The electrodes 76 are carried on the electrical lead 74 near the distal end. The electrodes 76 are electrically connected through the electrical lead 74 to the neuroelectrical stimulator 72. The electrodes 76 receive a stimulation signal 78 from the neuroelectrical stimulator 72 and convey this to an electrode 76 position within the patient's digestive system 22. The electrodes 76 can be configured as monopolar electrodes 76 with one electrode 76 per lead or as multipolar electrodes 76 with more than one electrode 76 per lead 74. The electrodes 76 are attached to the electrical lead 74 prior to implantation and navigated to a point near the desired stimulation site. The electrodes 76 are made from a biocompatible conductive material such as platinum-iridium. The electrodes 76 are implanted into the muscle wall of the stomach 26 such as 0.5 cm to 10.0 cm apart on the greater curvature at the limit of the corpus-antrum. The electrical lead 74 and electrical contacts 76 are selected with an impedance to produce a pulse current of about 5.0 mA.

The stimulation signal 78 has a frequency selected to increase pancreatic 30 secretion such as from about 3.0 pulses per minute to 6,000 pulses per minute. The stimulation signal 78 has a pulse width selected to influence pancreatic 30 secretion such as from about 0.01 mSec to 500.0 mSec. The stimulation signal 78 has a peak amplitude selected to influence pancreatic 30 secretion such as from about 0.01 mA to 100.0 mA. The stimulation signal 78 is charge balanced for biocompatibility. More specifically, the stimulation signal 78 can have the following parameters: amplitude necessary to obtain a current of about 5.0 mA; a pulse width of about 330 $\mu$Sec; a pulse frequency of about 14.0 Hz; and a cycle "on" of about 0.1 seconds and "off" of about 5.0 seconds.

Figure 6:
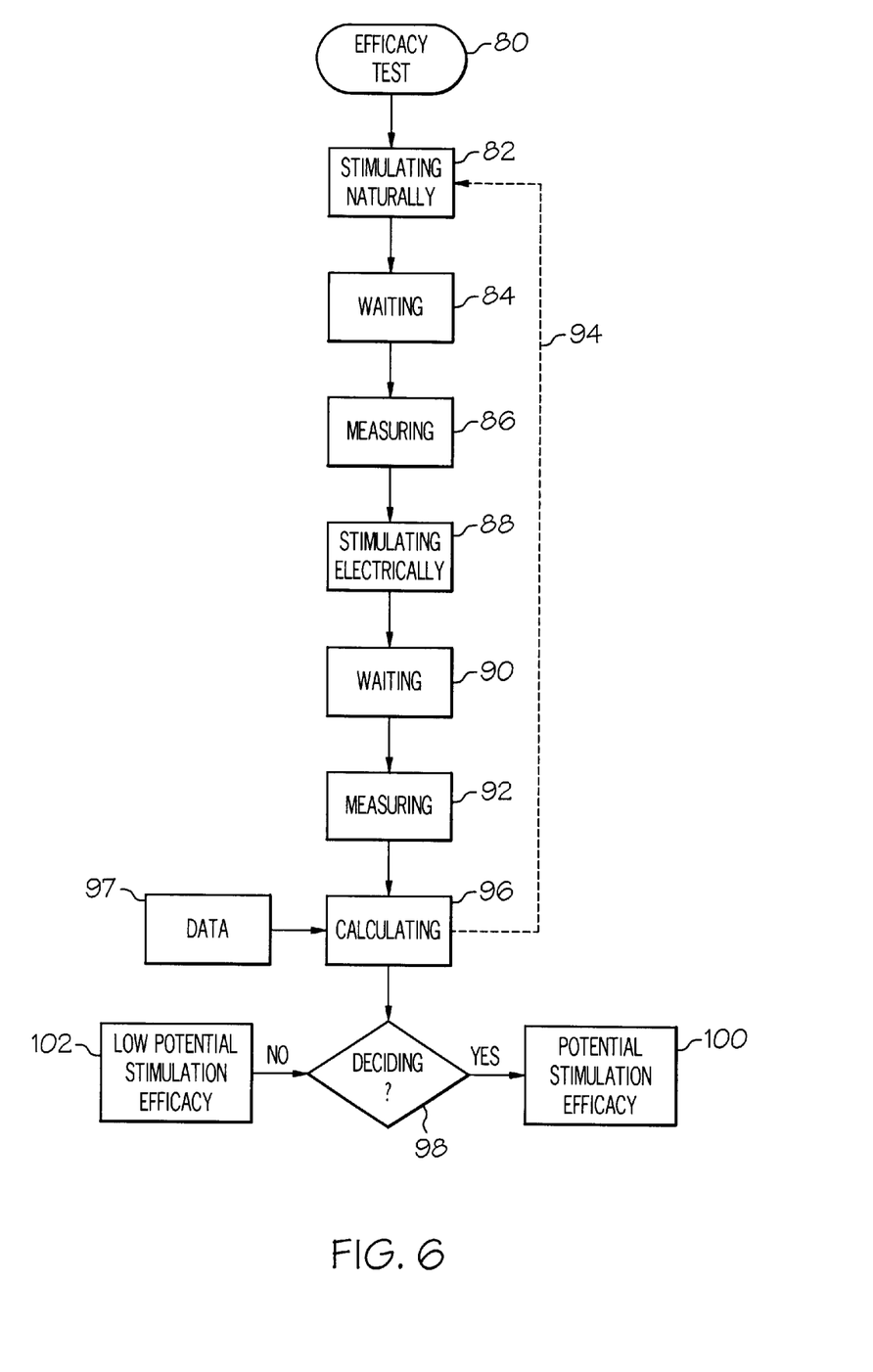
FIG. 6 shows a flow diagram for an efficacy test for gastroelectric stimulator to affect pancreatic secretion.

FIG. 6 shows a flow diagram of an efficacy test method for gastroelectric stimulation 80. The method 80 begins by naturally stimulating 82 the pancreatic 30 secretion of the patient 20 which is discussed in more detail above in the description under FIG. 3. After naturally stimulating 82 the patient 20, a natural response time is waited 84 which also is discussed in more detailed under FIG. 3. Next, pancreatic 30 response is measured 86 after waiting 84 the natural response time 84 which again is discussed in more detail under FIG. 3. After measurements 86 are taken, electrical stimulation 88 and natural stimulation 82 of the patient's pancreas 30 is done for a predetermined stimulation time such as in the range from 15.0 minutes to 24.0 hours. Electrical stimulation 88 is discussed in more detail earlier under FIG. 5. After electrical stimulation 88, natural stimulation 82 is continued, and an electrical response time is waited 90 such as described above in this paragraph, and measurements 94 are taken such as described above in this paragraph. Additionally, measurements 94 after natural stimulation 82 and after electrical stimulation 88 can be made after waiting predetermined time periods to establish more data points.

After the above measurements 86, 92 have been made, the differences between the pancreatic 30 response measured 86 after stimulating naturally 82 and waiting the natural response time 84 and after electrical stimulation 88 and waiting the electrical response time 90 are calculated 96. Calculations 96 can be simple or complex. Simple calculations 96 include such mathematical techniques as averaging the response indicator measurements 86, 92 over selected period of time or selecting the maximum value. Complex calculations 96 include such mathematical techniques as calculating the integral to find the area under the curve of the measurements 86, 92. Calculations 96 can also include the consideration of predetermined efficacy data 97 from previous test results from the patient undergoing the efficacy test 80, or predetermined efficacy data 97 can be available statistical information. Once calculations 96 are completed, a decision 98 can be made.

Deciding 98 whether there is potential efficacy 100 or low potential efficacy 102 in using gastroelectrical stimulation to treat pancreatic 30 conditions is done by examining the calculations 96. If the calculations 96 show increased pancreatic 30 secretion with electrical stimulation 88, then there is potential efficacy 100. If the calculations 96 show little or no increase in pancreatic 30 secretion with electrical stimulation 88, then there is low potential efficacy 102. As an example, electrical vagal stimulation on pigs has been found to increase pancreatic secretion by up to 5,200% in a study by Jens Holst et al., Nervous Control of Pancreatic Secretion in Pigs, Acta Physiol. scand. 105, 33–51 (1979).

Figure 7A:
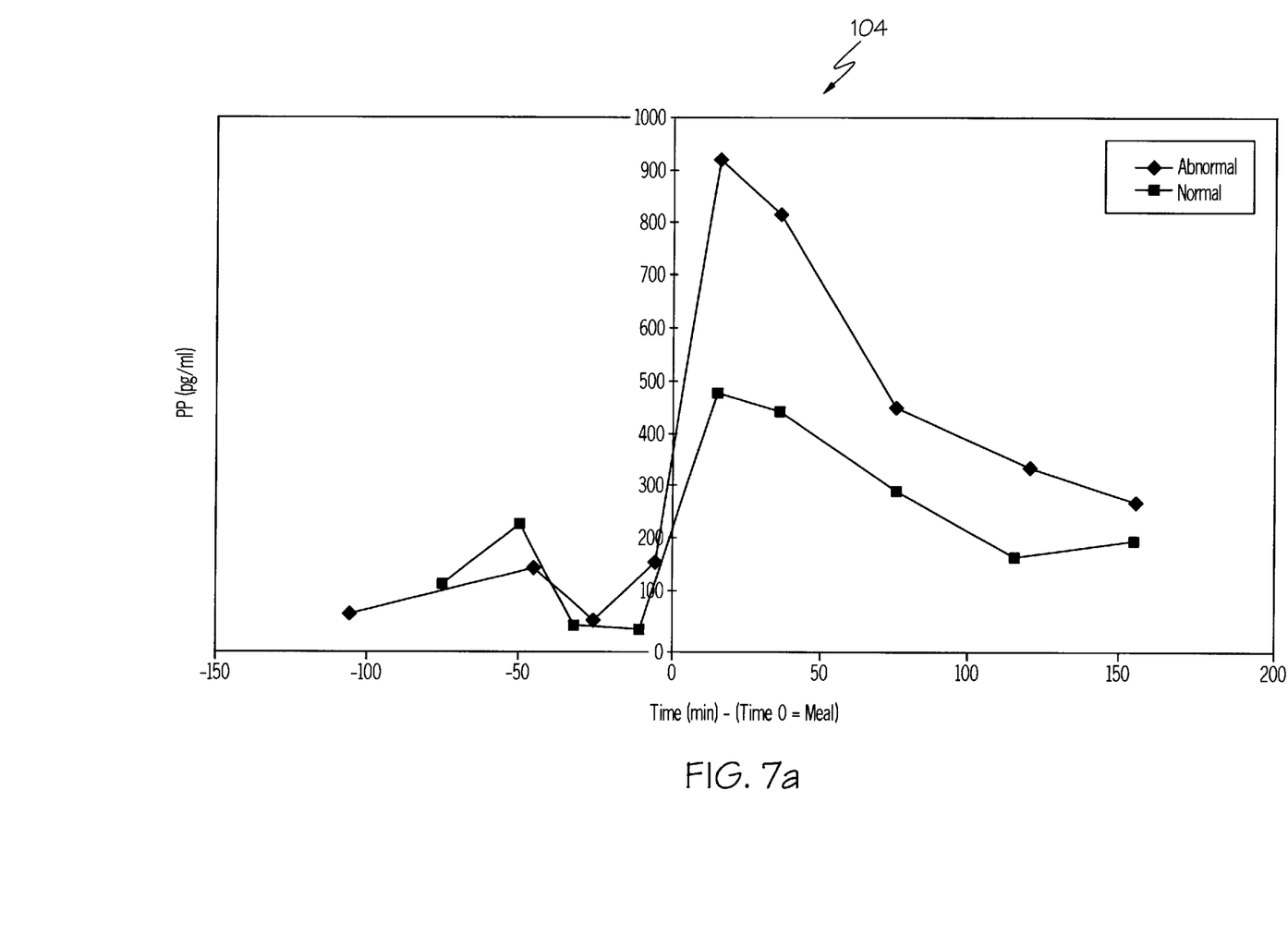
FIGS. 7a–b show graphs of results from the efficacy test for gastroelectric stimulation to affect pancreatic secretion.
Figure 7B:
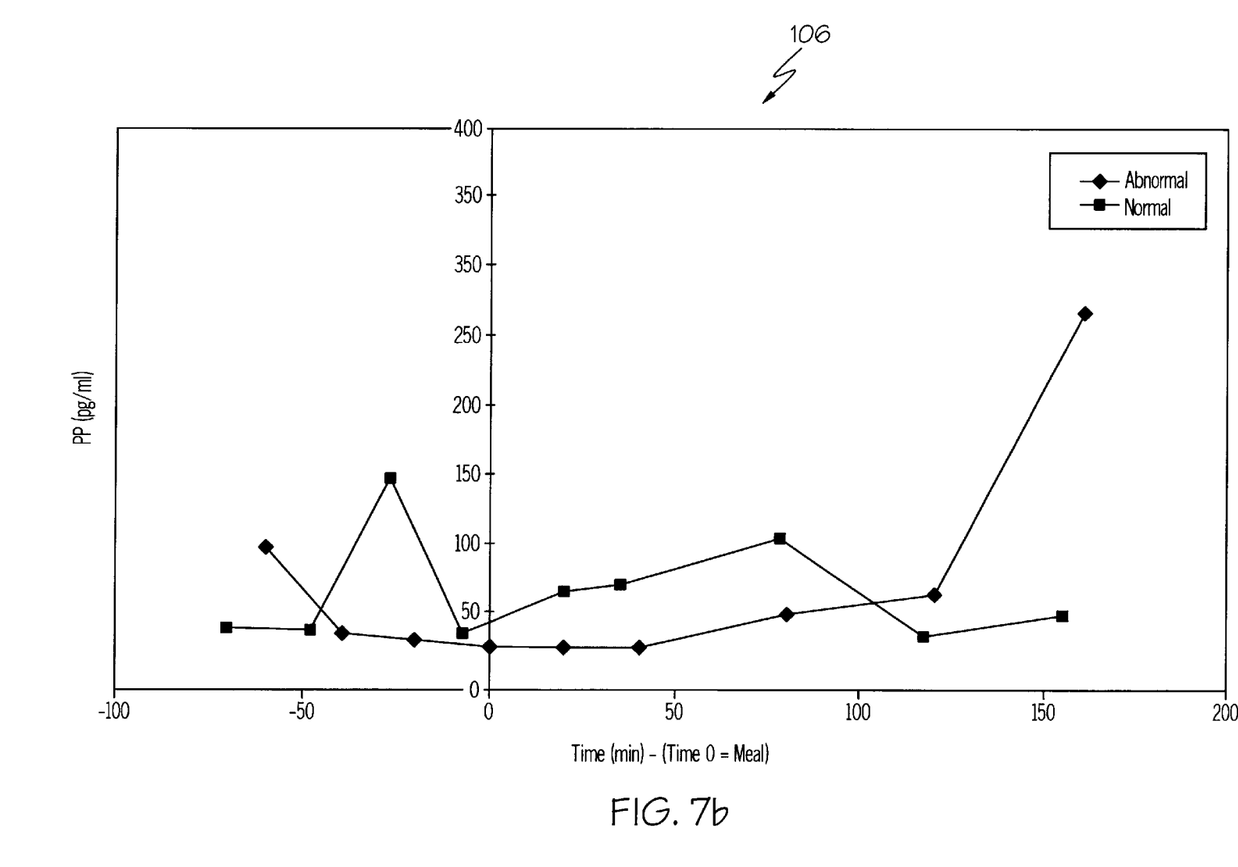

FIG. 7a shows results from a third patient 104 who underwent the screening test 42 in a first sequence 108 without electrical stimulation, and the efficacy test 80 in a second sequence 110 with electrical stimulation 88. FIG. 7*b* shows results from a fourth patient 106 who underwent the screening test 42 in a first sequence 108 without electrical stimulation, and the efficacy test 80 in a second in a second sequence 110. By plotting both sequences 108, 110 on the same graph, the potential efficacy of electrical stimulation 88 to affect pancreatic 30 secretion can be understood. The graphic information is arrayed in a similar fashion to the information in FIG. 4 with natural pancreatic 30 stimulation occurring 82 at t=0. In the second sequence 110 using electrical stimulation 88, the electrical stimulation 88 was generally applied as described above under FIG. 5. More specifically, the electrodes 76 were applied on the stomach 26, and the stimulation signal 78 current was 5.0 mA with a pulse width of 330.0 μSec. In FIG. 7*b*, the screening test 42 without gastroelectric stimulation, the elevation of polypeptide at about 155.0 minutes is not understood. The recorded elevation was likely a data collection error.

Figure 8:
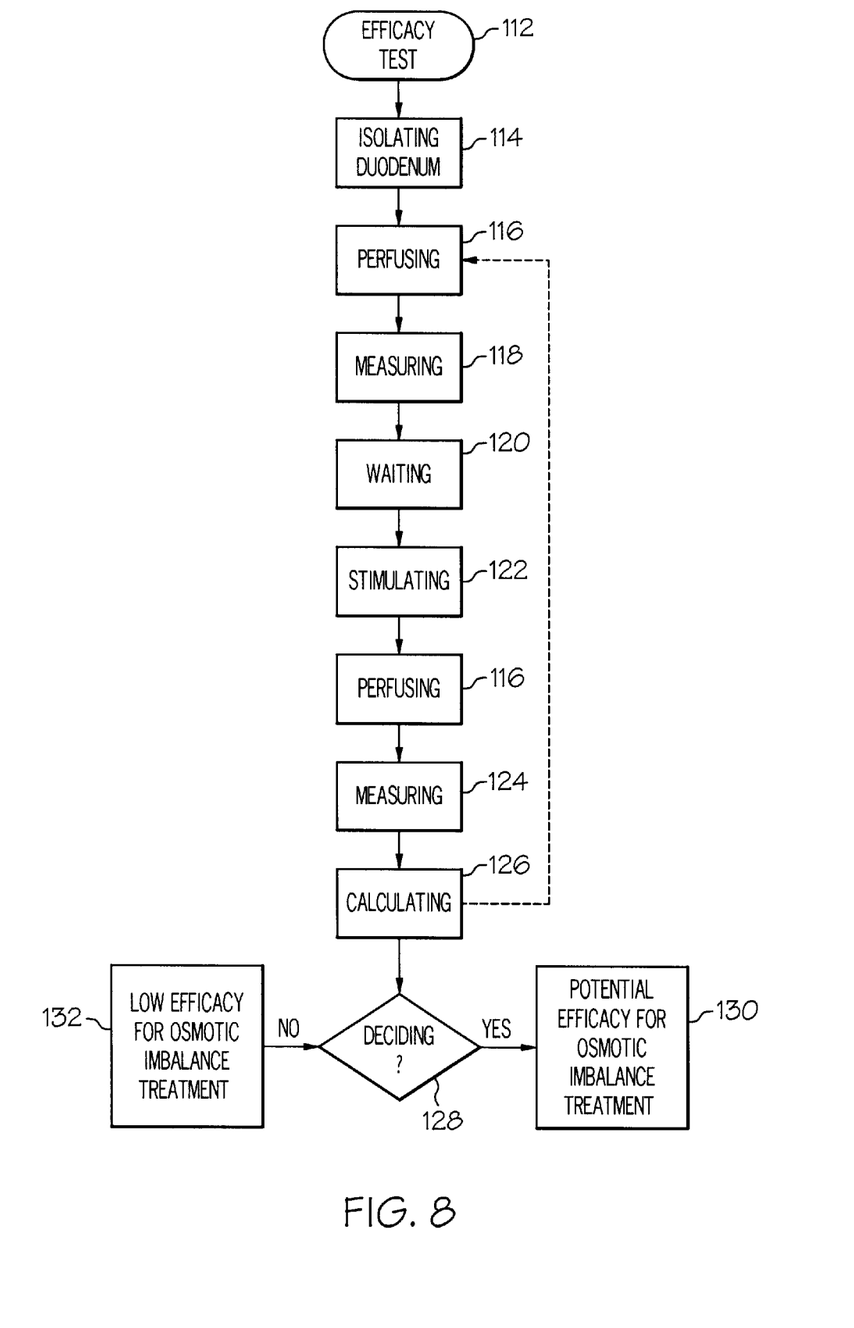
FIG. 8 shows a flow diagram for an efficacy test to use a gastroelectric stimulator to treat emesis.

FIG. 8 shows a flow diagram of an efficacy test 112 using a gastroelectric stimulator 44 to treat duodenal osmotic imbalance in a patient 20. The test 112 begins with isolating the patient's duodenum 114 near the pancreas 30 to create a duodenum isolation area 50 (FIG. 9) that substantially prevents fluid flow into or out of the isolation area 50. The duodenal isolation area 50 includes the hepatopancreatic ampulla 136 (FIG. 9). A detailed discussion of creating the duodenum isolation area 50 along with perfusion and draining with a catheter 134 is provided below under FIG. 9. After a duodenal isolation area 50 has been created 114, a solution is perfused 116 of increasing osmolity at predetermined infusion times into the duodenum isolation area 50. The perfused solution is composed of a carrier fluid such as distilled water and a chemical to reach the desired osmolity such as sodium chloride (NaCl) or glucose. The perfused solution can also include a non-absorbable marker such as polyethyleneglycol. The solution should typically increase in osmolity from about 100.0 mOsm/L to 1,000.0 mOsm/L in increments from about 50.0 ml to 500.0 ml. The perfusion 116 into the duodenal isolation area 50 will typically be from about 1.0 ml/minute to 10.0 ml/minute using an infusion pump. Osmolity should typically be increased by an osmotic increase time period of about every 15.0 minutes to 60.0 minutes. Before increasing osmolity, gastric juices should be aspirated, so osmolity can be better controlled by the infusate. Prior to beginning perfusion 116, the duodenum isolated area 50 can be washed with an isotonic solution to establish a baseline of osmolality. A marking solution can be perfused above the duodenal isolation area 50 to signal if fluid flows from above the duodenal isolation area 50 into the duodenal isolation area 50 to affect measurements. A more detailed discussion of the solution of increasing osmolity and perfusion is discussed below under FIG. 10.

During the perfusion 116 when the patient experiences nausea, a first duodenum osmolality level that causes nausea in the patient is measured 118 and recorded. After nausea is experienced by the patient, an osmotic decrease time 120 is waited that is sufficient for the osmolality of the duodenum isolation area 50 to reduce below the first duodenum osmolality level.

The patient's pancreas 30 is stimulated 122 using a gastroelectric stimulator 44 configured similar to that discussed under FIG. 5. Once again a solution of increasing osmolality is perfused 116 at the osmotic increase time period into the duodenum isolation area 50. Again, during the perfusion 116 when the patient experiences nausea, a second duodenum osmolality level that causes nausea in the patient is measured 124. The difference between the first duodenal osmolality level 118 and the second duodenal osmolality level 124 is calculated. Finally, a decision 128 is made whether gastroelectric stimulation has efficacy according to the difference between the first 118 and second 124 duodenal osmolality levels. Deciding whether there is potential efficacy 130 or low potential efficacy 132 in using gastroelectrical stimulation to treat pancreatic 30 conditions is done by examining the calculations 126. If the calculations 126 show increased pancreatic 30 secretion with electrical stimulation, then there is potential efficacy 130. If the calculations 126 show little or no increase in pancreatic 30 secretion with electrical stimulation 122, then there is low potential efficacy 132.

FIG. 9 shows a catheter 134 positioned to perform the efficacy test 112 to treat emesis. The patient is placed in a comfortable upright position and asked to refrain from swallowing saliva. Before the catheter 134 is inserted, a drainage tube is inserted into the stomach and the gastric juices are aspirated. The catheter 134 is inserted into the duodenum 28 with the help of an endoscope. To aid in insertion, the catheter's 134 tip and the two balloons 46, 48 are lubricated with lignocaine/lidocaine gel (2.0%) and a local anesthetic is used for the passage of the phyrynex. The catheter 134 is properly position when the hepatopancreatic ampulla 136 is between the two balloons 46, 48. The balloons 46, 48 are inflated under endoscopic control to a pressure adequate to isolate the duodenum area 50 but not inflated enough to cause abdominal pain and pressure should remain below blood pressure. Once the catheter 134 is properly inserted, the endoscope is removed.

Figure 10:
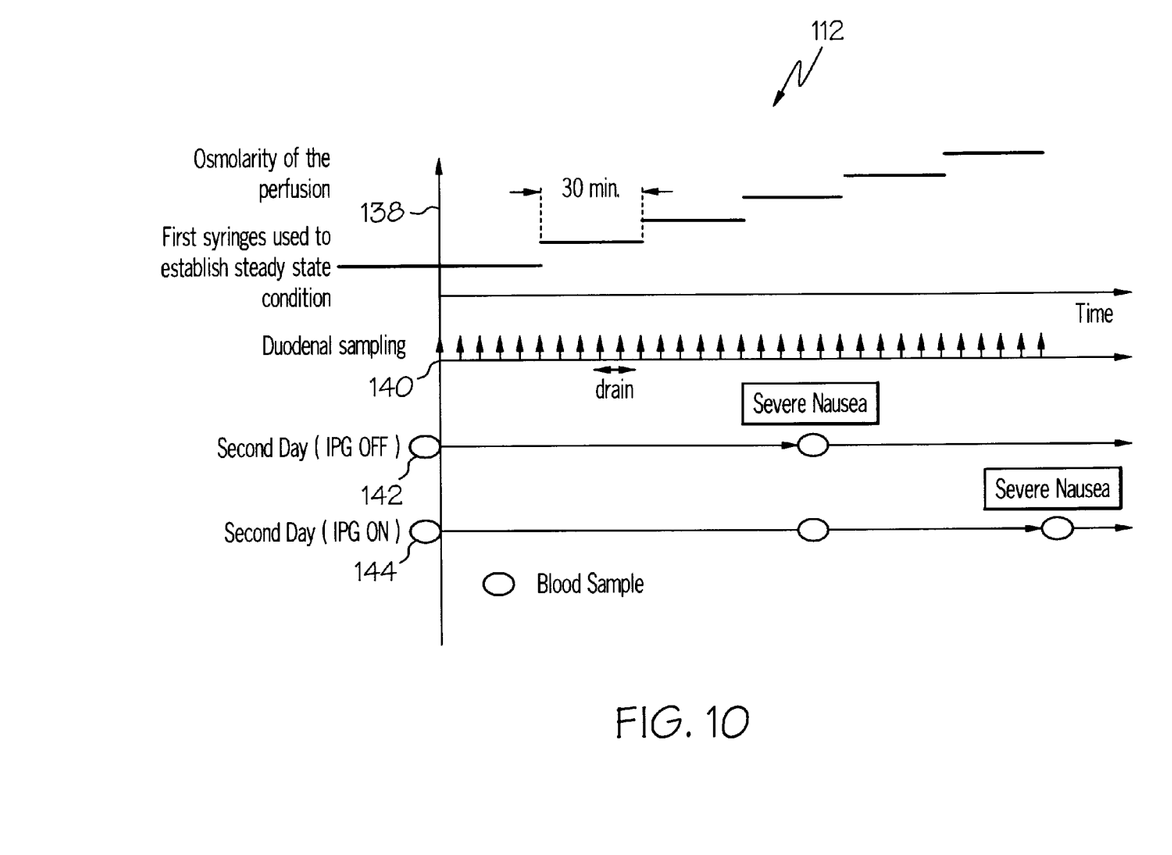

FIG. 10 shows a timing diagram of the efficacy test 112 to treat emesis. Blood pressure is monitored during the test 112. Seven syringes of about 150.0 ml are prepared with the following composition: distilled water, non-absorbable marker such as polyethyleneglycol, and NaCl concentrations varying such as 280.0, 280.0, 380.0, 480.0, 580.0, 680.0, and 780.0 mOsm/L. The contents of these syringes will be infused into the closed duodenal segment at a rate of 5.0 ml/min using an infusion pump. Every 30.0 minutes a new infusion syringe with a higher osmolality will be infused 138 and the gastric juices will be aspirated. The non-absorbable marker can also be a radiolabeled sodium to assist in distinguishing the how much perfusate is absorbed in the duodenal isolation area 50.

The duodenal isolation area 50 is washed with an isotonic solution (280.0 mOsml/L NaCl). The first syringe is then infused into the isolation area 50 (osmolality of 280.0 mOsml/L) to establish steady state conditions and to avoid a potential effect of the duodenum 28 distention on gallbladder emptying such as described in Fiorucci et al., "Duodenal Osmolality Drives Gallbladder Emptying in Humans, Digestive Diseases and Sciences", Vol. 35, No. 6, pp. 698–704 (June 1990). After each new syringe is infused 138 every 30.0 minutes, a blood sample is take, and duodenal samples are taken every 5.0 minutes 140 by gravity drainage and are labeled and frozen.

Above the isolation area 50, a 154.0 mM NaCl solution containing Phenol Red is perfused and drained to serve as a marker for potential infiltration of stomach 26 chyme into the isolated duodenal area 50 that could affect the measurement of duodenal 28 juice. The pressure in the proximal balloon 46 can be adjusted if necessary to maintain isolation. Likewise, if the volume of duodenal 28 sampling decreases during testing, distal balloon 48 pressure can be increased. When adjusting balloon 46, 48 pressures, the patient should be asked to confirm that the pressure is not causing abdominal pain.

For the first day of testing 142, the patient 20 is asked to indicate when she feels slight nausea (barely noticeable nausea), nausea, and severe nausea (imminent vomiting). When the patient indicates one of these conditions, the perfusion is stopped and the time and osmolity of the solution is recorded. Additionally, a blood sample can be taken when the perfusion is stopped. At the end of the test, an X-Ray is taken to confirm that the catheter 134 has not moved.

For the second day of testing 144, a gastroelectric stimulator 44, is used with a signal 78 similar to that discussed above under FIG. 5. The second day test 144 follows the protocol of the first day test 142 except that the gastroelectric stimulator 44 is turned on near the beginning of the test 144 when a steady state osmolality has been reached. It is believed that use of the gastroelectric stimulator 44 will delay the onset of slight nausea, nausea, and severe nausea until a substantially higher level of osmolality has been infused.

Chemical analysis of the blood and duodenal 28 samples should be performed as follows. The blood should be tested to determine the level of substances such as antidiuretic hormone (ADH), electrolytes, glucose (HbAlc), and polypeptide. The duodenal 28 samples should be tested to determine their osmolality and identify substances that assist in identifying the quantity of pancreatic 30 output and distinguish between pancreatic 30 output and biliary output such as polyethyleneglycol (to determine the volume secreted by the pancreas/bile), phenol red (to determine if the proximal balloon 46 seal was adequate), sodium, trypsin, and bile acids. Additionally, pancreatic 30 aspirate can be evaluated to determine if the pancreas 30 has been stimulated.

The testing protocol 112 can include other tests to relate physiological conditions to duodenal 28 osmolality. When duodenal 28 and blood samples are taken, stomach chyme could also be collected and analyzed to provide data on the normal osmolality of chyme that reaches the duodenal isolated area 50. An electrogastrogram (EGG) could be recorded to identify whether there is a correlation between nausea and gastric dysrhythmia.

Although the invention has been described in detail with reference to certain preferred versions, other versions are possible. Therefore the spirit and scope of the appended claims should not be limited to the description of the preferred versions described in this disclosure.

What is claimed is:

1. A screening test for using gastroelectric stimulation to affect pancreatic exocrine secretion in a patient, comprising:
    measuring a pancreatic response of a patient;
    stimulating naturally the pancreatic secretion of the patient;
    waiting a natural response time after the step of stimulating naturally the pancreatic secretion of the patient;
    measuring the pancreatic response after waiting the natural response time;
    calculating the difference between the pancreatic response measured before the step of stimulating naturally the pancreatic secretion of the patient and the step of waiting the natural response time after the step of stimulating naturally the pancreatic secretion of the patient;
    deciding whether there is potential efficacy in using a gastroelectric stimulator to affect pancreatic exocrine secretions in the patient by evaluating the difference calculated in the step of calculating the difference between the pancreatic response measured before the step of stimulating naturally the pancreatic secretion of the patient and the step of waiting the natural response time after the step of stimulating naturally the pancreatic secretion of the patient.

2. The screening test for gastroelectric stimulation as in claim 1, further comprising comparing the difference between the patient's pancreatic response measured before the step of stimulating naturally the pancreatic secretion of the patient and the pancreatic response measured after waiting the natural response time after the step of stimulating naturally the pancreatic secretion of the patient against predetermined screening data.

3. The screening test for gastroelectric stimulation as in claim 2 wherein the predetermined screening data are developed from statistical data on differences between the pancreatic response measured.

4. The screening test for gastroelectric stimulation as in claim 2 wherein predetermined data are developed for the patient by repeating the screening test at least two times on the patient.

5. The screening test for gastroelectric stimulation as in claim 1 wherein measuring pancreatic secretion is done with a specimen selected from the group consisting of: blood, duodenal pancreatic secretion, and stool.

6. The screening test for gastroelectric stimulation as in claim 5 wherein duodenal pancreatic secretion is measured by isolating the patient's duodenum with an upstream occlusion and a downstream occlusion to create an isolation area, evacuating duodenal pancreatic secretion from the isolation area, and measuring duodenal pancreatic secretion.

7. The screening test for gastroelectric stimulation as in claim 5 wherein pancreas response is measured by measuring a pancreatic secretion indicator in the specimen.

8. The screening test for gastroelectric stimulation as in claim 1 wherein the pancreatic response is measured by measuring a pancreatic exocrine secretion indicator.

9. The screening test for gastroelectric stimulation as in claim 8 wherein the pancreatic exocrine secretion indicator is selected from the group consisting of: fat, elastase, amylase, and lipase.

10. The screening test for gastroelectric stimulation as in claim 1 wherein the pancreatic secretion indicator is a pancreatic endocrine response indicator.

11. The screening test for gastroelectric stimulation as in claim 10 wherein the pancreatic endocrine response indicator is selected from the group consisting of: pancreatic polypeptide and insulin.

12. The screening test for gastroelectric stimulation as in claim 1 wherein the step of stimulating naturally the pancreatic secretion of the patient is selected from the group consisting of: smelling food and ingesting food.

13. An efficacy test for gastroelectric stimulation to affect pancreatic exocrine secretion in a patient, comprising:
    stimulating naturally a pancreas of a patient;
    waiting a natural response time;
    measuring a pancreatic response after waiting the first period of time;
    stimulating electrically the patient's pancreas with a stimulation signal and stimulating naturally the pancreas of the patient;
    waiting an electrical response time;
    measuring a pancreatic response in the patient's blood after waiting the electrical response time;
    calculating the difference between the pancreatic response measured after stimulating naturally and waiting the natural response time and the before stimulating naturally and the pancreatic response measured stimulating electrically the patient's pancreas and waiting the electrical response time; and, deciding the efficacy of gastroelectric stimulation to treat pancreatic exocrine conditions.

14. The gastroelectric stimulator as in claim 13 wherein there is efficacy when the pancreatic response measured after the first predetermined period of time is lower than the pancreatic response measured after the second predetermined period of time.

15. The gastroelectric stimulator as in claim 13 wherein there is low efficacy when the pancreatic response measured after waiting the natural response time is substantially the same as the pancreatic response measured after waiting the electrical response time.

16. An efficacy test for a gastroelectric stimulator to affect pancreatic exocrine secretions in a patient, comprising:
   providing a gastroelectric stimulator, comprising:
      a neuroelectrical stimulator for producing a stimulation signal;
      at least one electrical lead having a proximal end and a distal end, the proximal end being connected to the neuroelectrical stimulator and the distal end positionable in a lead position within the patient's abdomen; and,
      at least two electrodes carried near the electrical lead distal end, the electrodes being electrically connected through the electrical lead to the neuroelectrical stimulator to receive the stimulation signal and convey this signal to an electrode position within the patient's digestive system,
      wherein the stimulation signal is adapted to influence pancreatic exocrine output;
   stimulating naturally a pancreas of a patient;
   waiting a natural response time;
   measuring a pancreatic response after waiting the natural response time;
      stimulating electrically the patient's pancreas with a stimulation signal and
      stimulating naturally the pancreas of the patient;
   waiting an electrical response time;
   measuring a pancreatic response in the patient's blood after waiting the electrical response time;
   calculating whether the pancreatic response measured after stimulating naturally and waiting the natural response time is higher or lower than the pancreatic response measured stimulating electrically the patient's pancreas and waiting the electrical response time; and,
   deciding the efficacy of gastroelectric stimulation to treat pancreatic exocrine conditions.

17. The efficacy test for a gastroelectric stimulator as in claim 16 wherein electrodes are placed on the stomach.

18. The efficacy test for a gastroelectric stimulator as in claim 16 where the stimulation signal is 1.0 to 6,000 pulses per minute.

19. An efficacy test method for using a gastroelectric stimulator to treat duodenal osmotic imbalance in a patient, comprising:
   isolating the patient's duodenum near the pancreas to create a duodenum isolation area that substantially prevents fluid flow into or out of the isolation area;
   perfusing a solution of increasing osmolty at an osmotic increase time period into the duodenum isolation area;
   measuring a first duodenum osmolality level that causes nausea in the patient;
   waiting an osmotic decrease time sufficient for the osmolality of the duodenum isolation area to reduce below the first duodenum osmolality level;
   stimulating the patient's pancreas using a gastroelectric stimulator;
   perfusing a solution of increasing osmolality at the osmotic increase time period into the duodenum isolation area;
   measuring a second duodenum osmolality level that causes nausea in the patient;
   calculating the difference between the first duodenal osmolality level and the second duodenal osmolality level; and,
   deciding whether gastroelectric stimulation has efficacy for treating duodenal osmotic imbalance according to the difference between the first and second duodenal osmolality levels.

20. The efficacy test method as in claim 19, further comprising:
   perfusing a marking solution above the duodenum isolation area to signal if fluid flows from above the duodenum isolation area into the duodenum isolation area.

21. The efficacy test method as in claim 19 wherein perfusing a solution of increasing osmolality at the osmotic increase time period into the duodenum isolation area is accomplished with a sodium chloride (NaCl) solution of increasing osmolality.

22. The efficacy test method as in claim 21 wherein the sodium chloride solution increases in osmolality in the range from about 100 mOsml/L NaCl to 1,000 mOsml/L NaCl.

23. The efficacy test method as in claim 19 wherein perfusing a solution of increasing osmolality at the osmotic increase time period into the duodenum isolation area is accomplished with a glucose solution of increasing osmolality.

24. The efficacy test method as in claim 19 wherein the osmotic increase time period for increasing the osmolatity of the perfusing solution is in the range from about 15 minutes to 60 minutes.

25. The efficacy test method as in claim 19 wherein a rate for perfusing solution is in the range from about 1.0 ml/minute to 9.0 ml/minute.

26. The efficacy test method as in claim 19, further comprising: washing the duodenum isolated portion with an isotonic solution prior to perfusing to establish a baseline of osmolality.

27. The efficacy test method as in claim 19 wherein the duodenal isolation area contains the hepatopancreatic ampulla.

28. The efficacy test method as in claim 19 wherein the isolation area is created with an upstream occlusion and a downstream occlusion.

29. The efficacy test method as in claim 28 wherein the upstream occlusion and the downstream occlusion are balloons.

30. The efficacy test method as in claim 29 wherein the balloons are inflated to a pressure less than blood pressure.

31. The efficacy test method as in claim 19, further comprising: sampling the duodenal isolation area osmolality at predetermined sampling intervals during perfusing.

32. The efficacy test method as in claim 31 wherein the predetermined sampling interval are in the range from about every 1.0 to 10 minutes.

* * * * *